United States Patent
Pensado et al.

(10) Patent No.: US 10,317,332 B2
(45) Date of Patent: Jun. 11, 2019

(54) SYSTEM, APPARATUS OR METHOD FOR CHARACTERIZING PITTING CORROSION

(71) Applicant: Southwest Research Institute, San Antonio, TX (US)

(72) Inventors: Osvaldo Pensado, San Antonio, TX (US); Pavan Kumar Shukla, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 873 days.

(21) Appl. No.: 14/479,060

(22) Filed: Sep. 5, 2014

(65) Prior Publication Data

US 2016/0069789 A1    Mar. 10, 2016

(51) Int. Cl.
| | |
|---|---|
| *G01N 31/00* | (2006.01) |
| *G01N 17/04* | (2006.01) |
| *G01B 11/30* | (2006.01) |
| *G01B 11/22* | (2006.01) |
| *G01N 21/88* | (2006.01) |

(52) U.S. Cl.
CPC ........... *G01N 17/043* (2013.01); *G01B 11/22* (2013.01); *G01B 11/303* (2013.01); *G01N 21/88* (2013.01)

(58) Field of Classification Search
CPC ...... G01N 17/043; G01N 21/88; G01B 11/22; G01B 11/303
USPC .... 702/30; 252/62.52, 62.54, 301.19, 62.53; 324/213, 216, 228; 73/104
See application file for complete search history.

(56) References Cited

U.S. PATENT DOCUMENTS

| | | | | |
|---|---|---|---|---|
| 3,862,047 A | * | 1/1975 | Weltman | G01N 27/84 252/62.52 |
| 4,121,157 A | * | 10/1978 | Weltman | G01N 27/84 252/62.52 |
| 4,759,211 A | * | 7/1988 | Longley-Cook | G01N 21/91 252/301.19 |
| 4,859,943 A | * | 8/1989 | Evans | G01N 27/84 324/216 |
| 5,610,326 A | * | 3/1997 | Leost | G01B 1/00 73/104 |
| 6,077,418 A | * | 6/2000 | Iseri | G01N 17/043 204/404 |
| 6,415,044 B1 | * | 7/2002 | Simpson | G01B 21/30 382/108 |
| 6,792,357 B2 | | 9/2004 | Menon et al. | |

(Continued)

FOREIGN PATENT DOCUMENTS

| | | | |
|---|---|---|---|
| CN | 202631468 U | * | 12/2012 |
| CN | 203101234 U | * | 7/2013 |

(Continued)

OTHER PUBLICATIONS

Giesko, et al., "Laser Profilometers for surface inspection and profile measurement" (2007).*

(Continued)

*Primary Examiner* — Hyun D Park

(74) *Attorney, Agent, or Firm* — Grossman, Tucker, Perreault & Pfleger, PLLC

(57) ABSTRACT

The present invention relates to a system, apparatus or and method to quantify features of relatively small defects or anomalies on a selected surface. Such defects may be associated with localized corrosion, such as pitting, that takes place on the surface of a metal exposed to a metallic environment.

10 Claims, 19 Drawing Sheets

(56) References Cited

U.S. PATENT DOCUMENTS

| | | | |
|---|---|---|---|
| 7,481,098 B2* | 1/2009 | Robertson | G01N 1/2806 73/104 |
| 9,289,922 B2* | 3/2016 | King | B29C 35/0261 |
| 2007/0068605 A1* | 3/2007 | Statnikov | C21D 10/00 148/558 |
| 2007/0196190 A1* | 8/2007 | Bourne | B23Q 17/2233 409/131 |
| 2012/0160442 A1* | 6/2012 | Anderson | B22D 11/049 164/4.1 |
| 2014/0190239 A1* | 7/2014 | Minamitani | G01N 17/002 73/31.01 |

FOREIGN PATENT DOCUMENTS

| | | | | |
|---|---|---|---|---|
| JP | 60087959 A | * | 5/1985 | ........... B22D 11/108 |
| RU | 2121525 C1 | * | 11/1998 | |

OTHER PUBLICATIONS

Delfosse et al., "Surface roughness measurements as a method for tribological characterisation of ball bearings," Lubrication Science (2006).*

Suryawanshi et al., "Method of surface roughnes evaluation using ruby laser beam," Int J. of Engineering and Applications (2012).*

* cited by examiner

_SYSTEM, APPARATUS OR METHOD FOR
CHARACTERIZING PITTING CORROSION_

FIELD OF THE INVENTION

The present invention relates to a system, apparatus or method for characterizing relatively small defects or anomalies on a selected surface. Such defects may be associated with localized corrosion, such as pitting, that takes place on the surface of a metal exposed to a metallic environment.

BACKGROUND

There are many applications where it is important to quantify the extent of degradation that is or has occurred on a device. A metal surface which is exposed to a corrosive environment can experience at least two forms of corrosion. The first form of corrosion occurs relatively uniformly over the surface, and a second form is relatively localized. This localized form of attack is often described as pitting corrosion. Uniform corrosion can take a relatively long time to reduce the thickness of a body of material and mechanical strength. By contrast, pitting corrosion can lead to relatively rapid puncturing of a body of material which can more rapidly lead to part deterioration and loss of functionality.

Identification, counting, and accurately measuring geometric dimensions of corrosion-induced pits on metallic surfaces has been relatively challenging and time consuming. Available visual and non-visual techniques require manually focusing on individual pits, one pit at a time. Efficient techniques to identify, count, and measure geometric dimensions of pits are lacking, particularly for laboratory scale coupons ranging in dimensions up to few inches.

Metallic coupons are routinely used in corrosion experiments, in the laboratory and in the field, to characterize the effects of corrosion environments on materials of interest. If the material is susceptible to pitting corrosion in an environment under consideration, a variable number of pits develop on the coupon surface exposed to the environment. Quantifying the number of pits, the area and volume affected by pitting, the depth of individual pits, and the depth on the metal surface affected by pitting would be valuable to more efficiently characterize pitting corrosion and the severity of corrosive environments. While, as noted, it is possible to individually measure pits with microscopic techniques, these individual pit measurements are labor intensive, especially if there are numerous pits on a corrosion coupon. Furthermore, surface roughness of the coupon and its topography complicates accurate measurements of pits. An apparatus and method is needed to more efficiently characterize pitting corrosion while accounting for surface roughness and topography on laboratory scale coupons.

SUMMARY

The present disclosure is directed to a system, apparatus or method for identifying corrosion surface pits on a metal surface. The system, apparatus or method may therefore include the procedure of identifying a plurality of pits on said metal surface with a measuring device and assigning the plurality of pits a value of x, y, and z where x and y are positions on the metal surface, and z is the depth, wherein the metal surface has a surface incline and curvature. This is then followed by correcting for the presence of surface incline and curvature by initially fitting the values of x, y, and z into the following relationship:

$$z_{plane}(x,y) = a + bx + cx^2 + dy + ey^2 + fxy \qquad (1)$$

wherein the coefficients a, b, c, d, e and f are all real numbers and vary according to the incline and curvature of the metal surface. This may then be followed by identifying a collection of differences, $\Delta z = z_{meas} - z_{plane}$, that satisfy the expression below $$|\Delta z| = |z_{meas} - z_{plane}| \le z_o$$

where $z_{meas}$ is the measured value of the z coordinate at a given x, y location on the metallic surface and $z_{plane}$ is the value of z at that location according to equation 1, and $z_o$ is assigned a depth value ($= -d_{pit}$, with $d_{pit}$ defined as a negative number) that is selected to compensate for the precision of the measuring device and the surface roughness present and not due to corrosion. This may then be followed by mapping of relative pit depths, $\Delta z$, that are less than $d_{pit}$ into a two-dimensional matrix (M) wherein a value of $\Delta z$ of greater than $d_{pit}$ is ignored and assigned a value of zero and a value of $\Delta z$ of less than $d_{pit}$ is entered and mapped into said matrix. One may then distinguish and identify pit depths in the two-dimensional matrix associated with corrosion from those pit depths associated with surface roughness.

The present invention also relates to a system for identifying corrosion surface pits on a metal surface comprising:

a measuring device that provides output information identifying a plurality of pits on said metal surface with and assigns said plurality of pits a value of x, y, and z where x and y are positions on the metal surface and z is the depth, wherein said metal surface has a surface incline and curvature;

a processor connected to receive said output from said measuring device which:

(i) corrects for the presence of surface incline and curvature by initially fitting the values of x, y, and z into the following relationship:

$$z_{plane}(x,y) = a + bx + cx^2 + dy + ey^2 + fxy \qquad (1)$$

wherein the coefficients a, b, c, d, e and f are all real numbers and vary according to the incline and curvature of the metal surface;

(ii) identifies a collection of differences, $\Delta z = z_{meas} - z_{plane}$, that satisfy the expression below $$|\Delta z| = |z_{meas} - z_{plane}| \le z_o$$

where $z_{meas}$ is the measured value of the z coordinate at a given x, y location on the metallic surface and $z_{plane}$ is the value of z at that location according to equation (1), and $z_o$ is assigned a depth value ($= -d_{pit}$) that is selected to compensate for the precision of the measuring device and the surface roughness present and not due to corrosion;

(iii) maps pit depths that are less than $d_{pit}$ into a two-dimensional matrix (M) wherein a value of $\Delta z$ of greater than $d_{pit}$ is ignored and assigned a value of zero and a value of $\Delta z$ of less than $d_{pit}$ is entered and mapped into said matrix; and (iv) distinguishes and identifies pit depths in said two-dimensional matrix associated with corrosion from those pit depths associated with surface roughness.

BRIEF DESCRIPTION OF THE DRAWINGS

The preferred embodiments of the present invention will be described herein in conjunction with the drawings, where like designations denote like elements.

DETAILED DESCRIPTION

Figure 1A:
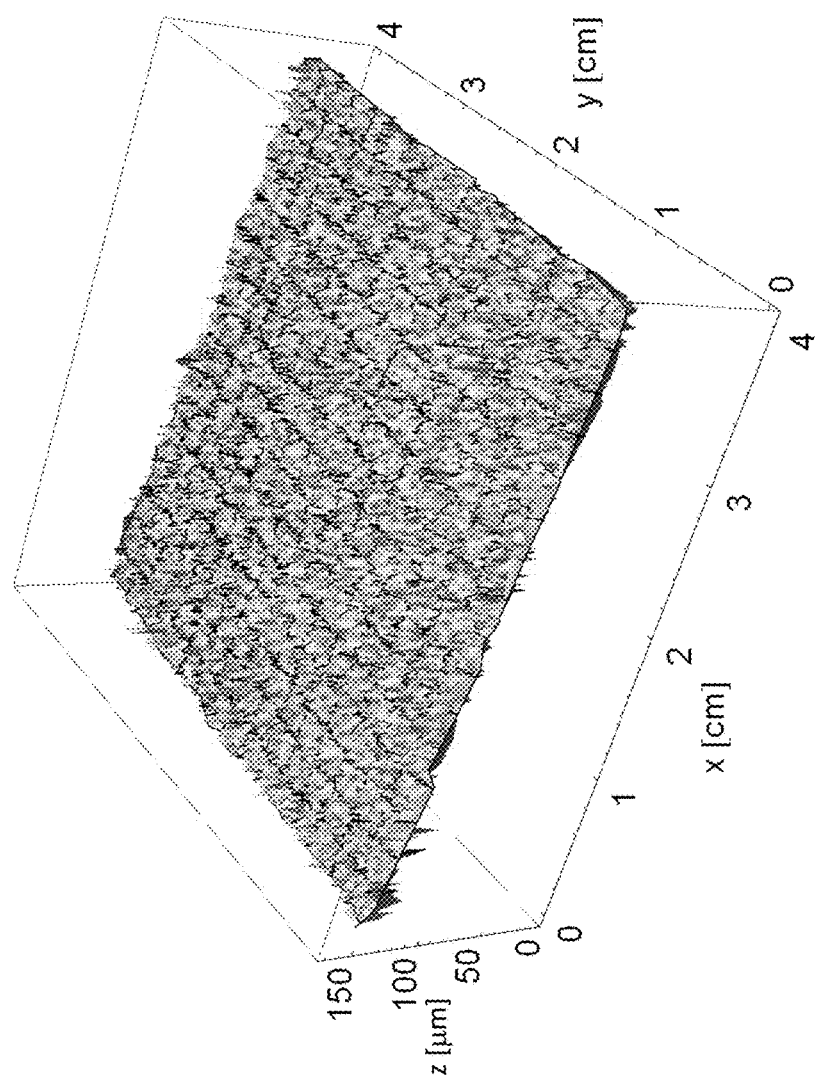
FIG. 1A shows an example of the raw data output by a laser profilometer.

The present invention relates to an apparatus and method for characterizing relatively small defects or anomalies on a selected surface. Preferably, one employs a profilometer which is a device that is capable measuring a surface profile and quantifying its roughness and surface features (e.g., physical features such as the number, depth and area of pits). A profilometer may therefore include a contact profilometer wherein a stylus is moved vertically in contact with a sample and then laterally across the sample a specified distance at a specified contact force, or a laser (non-contact) profilometer, which can operate at relatively high scan speeds, with improved reliability (the surface is not damaged by contact) and spot size or lateral resolution can range from a few microns to sub microns evaluation. It is also contemplated herein that one may use a fiber-based optical profilometer, where one relies upon an optical probe which sends light interference signals back to the profilometer detector via an optical fiber. The profilometer that was employed herein was obtained from Pacific Precision Laboratories, Inc., Chatsworth, Calif., Model: ZSCOPE, model no. 010-4003-001.

Accordingly, one preferably employs a laser profilometer and measures the surface profile of one or more metallic surfaces that has been exposed to a given corrosive environment. Preferably, the metallic surface amounts to a metallic coupon which may be understood as a metallic test sample that has the same composition of a metallic surface that is being evaluated and which has been exposed to a corrosive environment to replicate or simulate the environment under consideration. This then is followed by application of a pattern recognition process to analyze the profilometry data and extract information on pitting corrosion from the data.

As will be explained more fully herein, the pattern recognition procedure serves as a data filtration method to discount profilometry spikes when isolated and highlight spikes when grouped. Isolated profilometry spikes are typically related to original surface roughness, while grouped spikes could indicate pitting corrosion. By now mapping such grouped spikes into a 2-dimensional array, a view of the coupon surface can be produced that identifies the relative position of pits and ignores surface roughness and shallow features.

Once the profilometry data associated with pitting corrosion is now isolated, additional information can be extracted including but not limited to one or more of the following: (i) the number of pits; (ii) distributions of pit depths; (iii) separation of deep pits (e.g. pits associated with corrosion) from shallow pits and/or shallow topographic features (e.g. pits or projections on the surface that are not associated with corrosion or which fall within the noise background of a selected profilometer); (iv) total surface and volume affected by localized corrosion.

The present invention will now be described in detail as applied to a working example that considers the pitting corrosion on 304 stainless steel (SS) coupons. Pitting corrosion was induced by depositing a layer of sea-salt on the coupons and then placing them in a humidity chamber. Coupons of dimensions 5 cm×5 cm made of 304 SS were polished to remove manufacturer surface treatments which are typically used to enhance corrosion resistance. The 304 SS coupons were sprayed with simulated sea-salt solution. A simulated sea-salt layer was therefore deposited on the coupons after spraying of the sea salt solution and drying of the coupons at 95° C. for 10 minutes and repeating the cycle, spraying and drying six times. After the salt layer was deposited, additional simulated sea-salt salt was added on the surface of the coupons with a small spoon. The amount of the salt on the coupons ranged between 1.2 to 1.7 g. The coupons were placed in a humidity chamber, controlling the absolute humidity to approximately 30 g/m³ at 50° C. The pitting corrosion initiated within a couple of hours. The coupons were removed from the chamber to analyze pitting corrosion as described below.

The profilometer was programmed to sweep an area of 4 cm×4 cm, following lines detecting points in 10 µm increments, and spacing between lines also in 10 µm increments (i.e., the scan points are corners of squares 10-µm in length). The profilometer output data was then processed to correct for surface topography such as a surface incline and the presence of spurious readouts caused by surface roughness and profilometer artifacts.

Figure 1B:
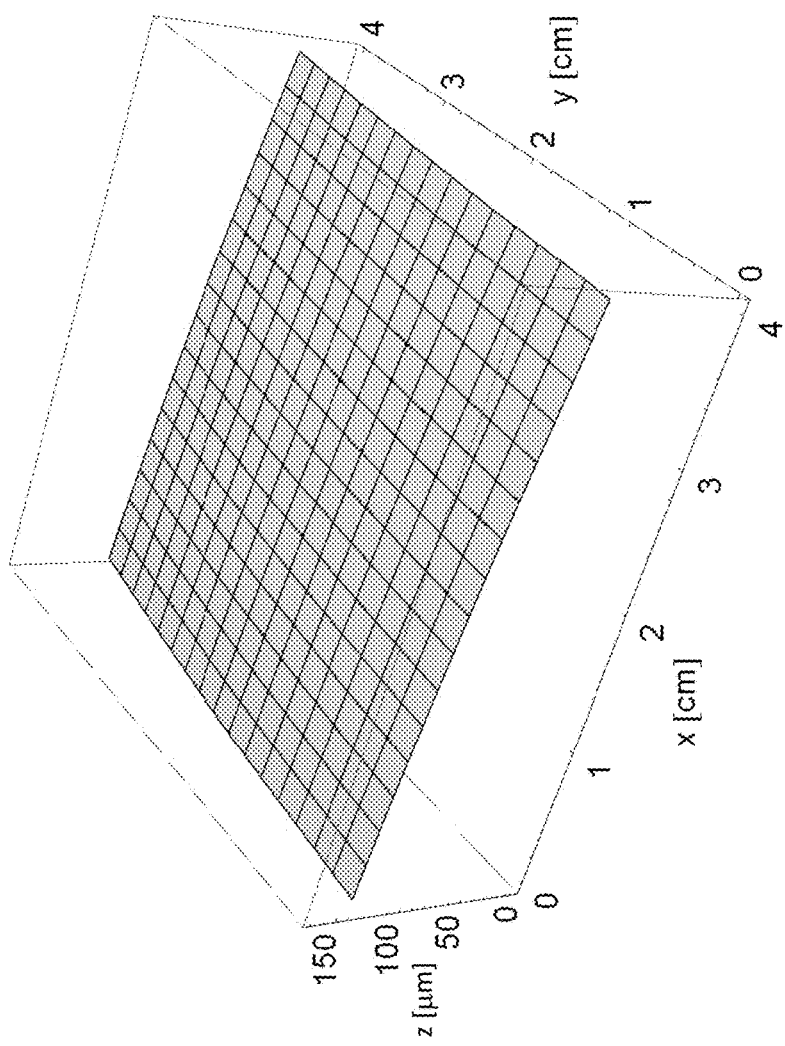
FIG. 1B is a fit of equation (1) to the raw data in FIG. 1A that makes evident the surface incline and surface curvature.

FIG. 1A shows an example of a plot of the raw data output by the laser profilometer. FIG. 1B is the plane resulting from fitting equation (1) to the raw data that makes evident the surface incline and surface curvature. The profilometer records all positive and negative spikes associated with roughness and lack of focusing artifacts. To more reliably identify corrosion pits from the profilometry readouts the data are filtered.

Data filtration initially proceeds by recognizing that the output of the laser profilometer is a file with points (x, y, z), where x and y are positions on the metal coupon, and $z_{meas}$ is the measured depth. Step 1 is a correction for surface incline and curvature. A quadratic plane of the form $$z_{plane}(x,y)=a+bx+cx^2+dy+ey^2+fxy \quad [1]$$

was fit to the profilometry data. FIG. 1B is an example of such a plane fit. In the above equation, the coefficients a, b, c, d, e and f are all real numbers and will vary according to the average incline and curvature of the coupon surface. Accordingly, equation [1] will conveniently define the reference surface that is now relied upon towards the goal herein of distinguishing and identifying corrosion pits on a given metallic surface. In the example in FIG. 1B, the resulting equation was $z_{plane}$=134.021−3.868 x−1.051 $x^2$−5.924 y−0.985 $y^2$−0.45 x y, with x and y measured in centimeters, and the resulting $z_{plane}$ in units of microns. This example equation was derived by a standard least squares method, by finding the coefficients a, b, c, d, e and f that minimize the total square residual, S, computed as $$S = \sum_{i=1}^{n} [z_i - z_{plane}(x_i, y_i)]^2 \quad [2]$$

where n is the number of data points considered in the fit (which is preferably a subset of the total number of points output by the profilometer that is well spread over the coupon surface to detect incline and curvature variations), and the triplets ($x_i$, $y_i$, $z_i$) are the profilometer outputs.

It is next recognized that the difference between the z coordinate of the profilometer output, $z_{meas}$, and $z_{plane}$ provides a correction for the presence of the metallic surface incline and curvature established above. The differences $z_{meas}-z_{plane}$ are relative depths with respect to the surface plane. Positive differences $z_{meas}-z_{plane}$ correspond to points located above the plane which are associated with surface roughness and spurious readouts. These above-the-plane points are dismissed in the present analysis, as later discussed. Negative differences $z_{meas}-z_{plane}$ are potentially associated with pits as explained more fully below depending upon the depth that is observed and the profilometer sensitivity.

It was observed that the collection of differences, $\Delta z = z_{prof} - z_{plane}$, that satisfy the expression below $$|\Delta z|=|z_{meas}-z_{plane}|\le z_o \quad [3]$$

approximately follows a normal distribution with a zero average, when $z_o$ was approximately 20 μm. In equation [3] above, $z_{meas}$ is the measured value of the z coordinate at a given x, y location on the metallic surface by the profilometer and $z_{plane}$ is the value of z at that location according to equation [1], and $z_o$ is a discriminating value of pit depth (=−$d_{pit}$) that is selected to compensate for the precision of the profilometer and the surface roughness that may be present and not due to corrosion.

The findings above were then interpreted to mean that |Δz| values in equation [3] that fall within the range −20 μm≤Δz≤20 μm are typically the result of profilometer noise and metal surface roughness. In other words, in the example, the laser profilometer would not generally distinguish features of dimensions (either pits or spikes) of less than or equal to 20 μm from noise. It may therefore now be appreciated that after the surface incline and curvature is established according to equation [1], and the value of $z_o$ in equation [3] is determined for a given surface and profilometer precision, pitting due to surface corrosion may be more reliably determined. Or, stated another way, after the surface incline and curvature is determined, and the precision of the laser profilometer is considered, and the metal surface roughness is determined (i.e. roughness not due to corrosion) an evaluation of pitting due to corrosion may proceed as discussed below.

Accordingly, identification of depths less than −20 μm (Δz≤−20 μm) are then mapped into a mathematical 2-dimensional (2D) representation (such as a matrix (M) of 500×500 entries) of the metallic surface. Accordingly, each of the 250,000 entries in such selected matrix corresponds to a square pixel of dimensions 80 μm×80 μm. Each pixel could enclose a maximum of 64 profilometry readouts (the profilometer was programmed to read depths in a selected grid such as a grid with 10 μm×10 μm spacing). A readout Δz>−20 μm (e.g., −10 μm, −5 μm, 0 μm, 100 μm, et cetera) is ignored by assigning a value of 0. Readouts Δz<−20 μm (e.g., −25 μm, −50 μm, −70 μm, et cetera) are tracked in the 2D matrix. Accordingly the matrix M will include values of 0 or a value of less than −20 μm. If a pixel encloses multiple profilometer readouts, then the pixel was given the deepest value of the enclosed readouts. For example, if a pixel enclosed the readouts 10 μm, −2 μm, −15 μm, then such pixel would be assigned a value of 0 μm, as all readouts are greater than −20 μm. A pixel enclosing the values −50 μm, −30 μm, 10 μm, 100 μm would be assigned a value of −50 μm as such value corresponds to the deepest readout.

Figure 2C:
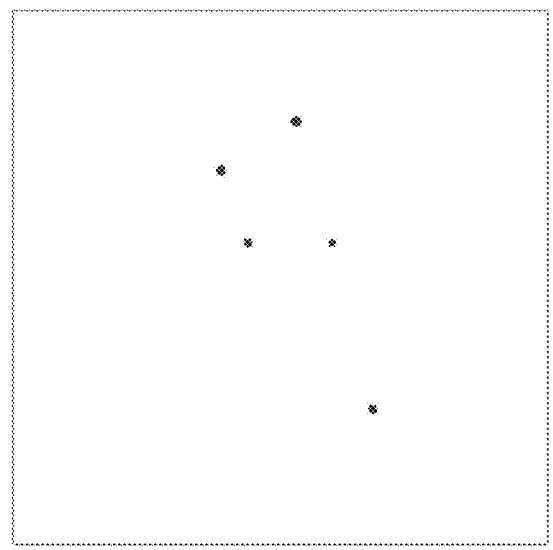
FIG. 2C is a filter image detecting clusters of pixels associated with corrosion pits.
Figure 2B:
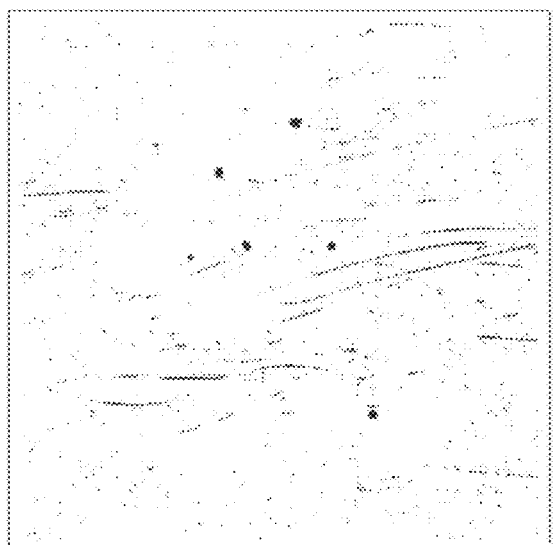
FIG. 2B is the laser profilometer output (density matrix plot) corrected for surface incline and ignoring relative depths of less than 20 µm.
Figure 2A:
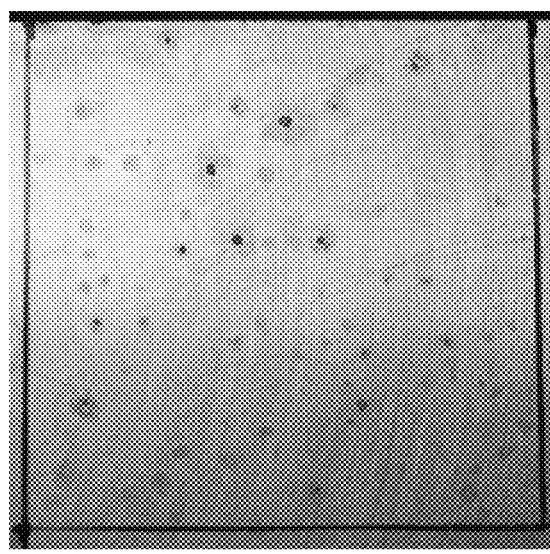
FIG. 2A is a photograph of a 4 cm×4 cm area of the metallic coupon.

FIGS. 2A, 2B and 2C provide an example of the transformation sequence. FIG. 2A is a photograph of a 4 cm×4 cm portion of the metallic coupon. FIG. 2B is a matrix density plot of the matrix after the data filtration; i.e. after determination of the surface incline and mapping of all depths of less or deeper than −20 μm, as described above. Pixels toned white were associated with values of zero and associated with profilometer readouts satisfying Δz≥−20 μm. The colored pixels correspond to pixels that enclose at least one profilometer readout satisfying Δz<−20 μm. This matrix of pixels may be denoted $M_1$. The matrix in FIG. 2B contains numerous isolated pixels that are associated with coupon surface roughness and not with pitting corrosion. Corrosion pits were next identified by clusters of the colored pixels. The next step in the process is directed at distinguishing clusters of pit depths and associated pixels in the matrix M associated with corrosion from isolated pixels most likely associated with surface roughness.

The identification of pixels associated with corrosion was accomplished by mapping the matrix into a second matrix ($M_2$) with 1 and 0 entries, depending on whether or not an entry in the matrix M was non-zero or zero (the size of the matrix $M_2$ is also 500×500). The operation to transform M into a matrix with 1 and 0 entries is denoted as:

$$M_2=|Sign(M)| \quad [4]$$

where the Sign function is applied entry-by-entry, and yields −1, 0, or 1 depending on whether an entry is negative, zero, or positive. The absolute function |·| is the positive value of a number, applied entry-by-entry in equation [4]. For example, using a small 3×3 matrix to clarify concepts, if the matrix M was defined as $$M = \begin{pmatrix} -30 & 0 & -25 \\ 0 & -100 & 0 \\ 0 & 0 & -50 \end{pmatrix} \quad [5]$$

then Sign(M) would be $$\text{Sign}(M) = \begin{pmatrix} -1 & 0 & -1 \\ 0 & -1 & 0 \\ 0 & 0 & -1 \end{pmatrix} \quad [6]$$

and $$M_2 = |\text{Sign}(M)| = \begin{pmatrix} 1 & 0 & 1 \\ 0 & 1 & 0 \\ 0 & 0 & 1 \end{pmatrix} \quad [7]$$

In other words, entries in $M_2$ equal to 1 are associated with entries that are non-zero in M. The purpose of the $M_2$ matrix is to facilitate identification of clustered entries with non-zero values.

The next step is using a moving average to highlight clusters of 1-entries in $M_2$, and define as zero entries that are isolated. The following operations in equations [8] and [9] are applied in iterative manner $$M_3 = \text{Moving Average}(M_2) \quad [8]$$

with a moving average applied along rows or columns, and a moving average window of 7 pixels, and $$M_2 = \text{Sign}[\text{Floor}(2 \times M_3)] \quad [9]$$

The moving average in equation [8] is computed along rows or columns of the matrix $M_2$. The matrix $M_3$ is defined also of dimension 500×500, requiring the addition of three or less zero entries to the edges of the matrix, so that the average is located at the center of the moving window.

To explain the actions of the operations in equations [8] and [9], and the inclusion of additional zero entries, a simplified example is presented with a 4×4 matrix. Consider a matrix $M_2$ as $$M_2 = \begin{pmatrix} 1 & 1 & 1 & 1 \\ 1 & 0 & 1 & 1 \\ 0 & 1 & 0 & 1 \\ 0 & 0 & 0 & 1 \end{pmatrix} \quad [10]$$

and perform a moving average along the horizontal direction, with a window of 7 entries. Starting on the first row, to define a 7-element average on the first entry (1,1), three zeroes are added to the left of the row vector: (0, 0, 0, 1, 1, 1, 1). The average of this extended vector is 4/7. The associated extended vector for the (1,2) entry is (0, 0, 1, 1, 1, 1, 0), and the average is also 4/7. Similarly for the (1,3) and (1,4) entries, the extended vectors are (0, 1, 1, 1, 1, 0, 0) and (1, 1, 1, 1, 0, 0, 0), respectively, and in both cases the averages are also 4/7. Moving to the second row, the extended 7-element vector for the (2,1) entry is (0, 0, 0, 1, 0, 1, 1), which average is 3/7. The extended vectors for the (2,2), (2,3), and (2,4) entries are (0, 0, 1, 0, 1, 1, 0), (0, 1, 0, 1, 1, 0, 0), and (1, 0, 1, 1, 0, 0, 0), which averages are all equal to 3/7. Continuing with this approach, the moving averages on the third row are all 2/7, and the moving averages on the fourth row are all 1/7. In summary, the result of the entry-by-entry moving average operation, with a 7-element window is $$M_3 = \text{Moving Average Over Rows}(M_2) = \begin{pmatrix} 4/7 & 4/7 & 4/7 & 4/7 \\ 3/7 & 3/7 & 3/7 & 3/7 \\ 2/7 & 2/7 & 2/7 & 2/7 \\ 1/7 & 1/7 & 1/7 & 1/7 \end{pmatrix} \quad [11]$$

Multiplying by 2 the matrix $M_3$, as called by Equation [9]:

$$2 \times M_3 = \begin{pmatrix} 8/7 & 8/7 & 8/7 & 8/7 \\ 6/7 & 6/7 & 6/7 & 6/7 \\ 4/7 & 4/7 & 4/7 & 4/7 \\ 2/7 & 2/7 & 2/7 & 2/7 \end{pmatrix} \quad [12]$$

The Floor function in equation [9] is applied entry-by-entry, and rounds a number to the closest lower integer. For example, Floor(8/7)=1; Floor(6/7)=0. Applying the Floor function, entry-by-entry as in equation [9], to equation [12] results in $$\text{Floor}(2 \times M_3) = \begin{pmatrix} 1 & 1 & 1 & 1 \\ 0 & 0 & 0 & 0 \\ 0 & 0 & 0 & 0 \\ 0 & 0 & 0 & 0 \end{pmatrix} \quad [13]$$

Further iterative application of equations [8] and [9], always produces the same output matrix, equation [13]. Similarly, if equations [8] and [9] were applied along the vertical direction or columns, the result would be $$\text{Floor}(2 \times M_3) = \begin{pmatrix} 0 & 0 & 0 & 1 \\ 0 & 0 & 0 & 1 \\ 0 & 0 & 0 & 1 \\ 0 & 0 & 0 & 1 \end{pmatrix} \quad [14]$$

Therefore, equations [8] and [9] preserve entries where at least 4 non-zero pixels are present along rows or columns in a 7-element window, and transform entries to zero if 3 or fewer non-zero pixels are enclosed in the 7-element window. The size of the moving average window can be made bigger to preserve only larger clusters of pixels. The moving average window size should be an odd number (e.g., 5, 7, 9, 11, et cetera).

The information in the matrices in equations [13] and [14] can be further combined by performing an entry-by-entry multiplication of the two matrices:

$$\begin{pmatrix} 1 & 1 & 1 & 1 \\ 0 & 0 & 0 & 0 \\ 0 & 0 & 0 & 0 \\ 0 & 0 & 0 & 0 \end{pmatrix} * \begin{pmatrix} 0 & 0 & 0 & 1 \\ 0 & 0 & 0 & 1 \\ 0 & 0 & 0 & 1 \\ 0 & 0 & 0 & 1 \end{pmatrix} = \begin{pmatrix} 0 & 0 & 0 & 1 \\ 0 & 0 & 0 & 0 \\ 0 & 0 & 0 & 0 \\ 0 & 0 & 0 & 0 \end{pmatrix} \quad [15]$$

The symbol * denotes entry-by-entry matrix multiplication. The only entry equal to 1 in resulting matrix in equation [15] indicates the "center" of the cluster of pixels that are non-zero in the input matrix in equation [10]. This 1 entry is identified as the potential center of a pitting corrosion site. Summarizing, if a non-zero entry in the matrix $M_2$ is surrounded by zeroes, the moving average for that entry yields a value less than one, which is rounded to zero after application of the operations in equation [9]. If an entry is surrounded by ones in $M_2$, the moving average yields values close or equal to one, which is left as one after application of equations [8] and [9]. By iterative application of equations [8] and [9], the only entries with 1 values in $M_2$, after the iterative sequence, are clustered and likely associated with pitting corrosion locations. An example of the resulting matrix, after iterating along horizontal and vertical directions, and performing a matrix product as in the example in equation [15] is presented in FIG. 2C.

The resulting matrix of 0 and 1 entries, $M_3$, is used as a filter. The pit depths are isolated by computing the product of $M_3 * M$ where the symbol * denotes entry-by-entry matrix multiplication. For example, in the 4×4 matrix example, if the matrix M was $$M = \begin{pmatrix} -25 & -31 & -52 & -60 \\ -22 & 0 & -25 & -51 \\ 0 & -23 & 0 & -30 \\ 0 & 0 & 0 & -23 \end{pmatrix} \quad [16]$$

entry-by-entry multiplication of the matrix M by the filter matrix $M_3$ in equation [15] yields $$M_3 * M = \begin{pmatrix} 0 & 0 & 0 & -60 \\ 0 & 0 & 0 & 0 \\ 0 & 0 & 0 & 0 \\ 0 & 0 & 0 & 0 \end{pmatrix} \quad [17]$$

In other words, only one pixel is isolated as candidate for pitting corrosion in this example, with a depth of 60 μm. In the example shown in FIGS. 2A, 2B and 2C, the identified five pits enclosed a total of 314 pixels. Each pixel is a record of a maximum depth in a square of dimensions 80 μm×80 μm.

Figure 3B:
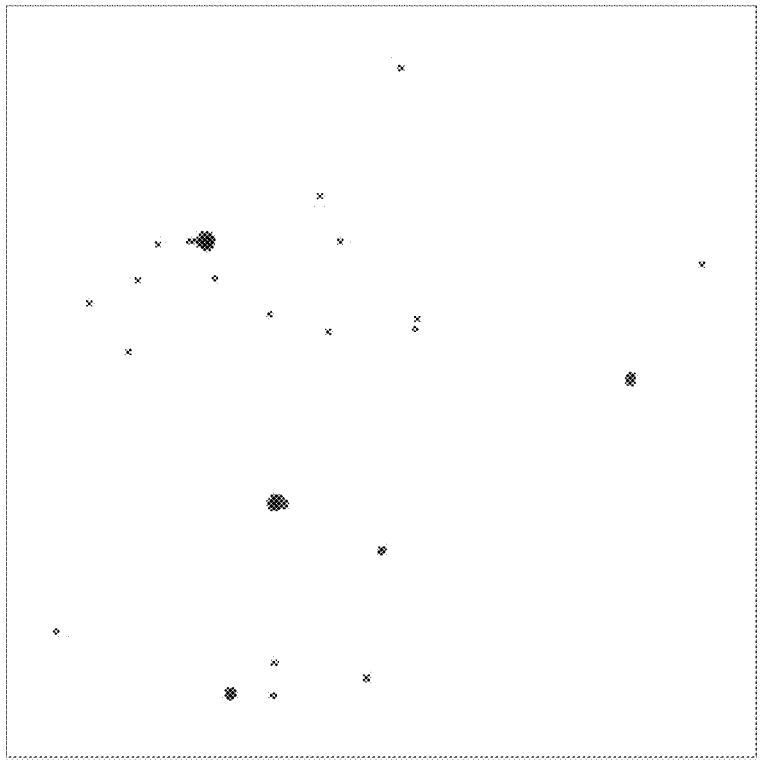
FIG. 3B is the outcome of applying the filtration algorithm $M_3*M$ on FIG. 3A.
Figure 3A:
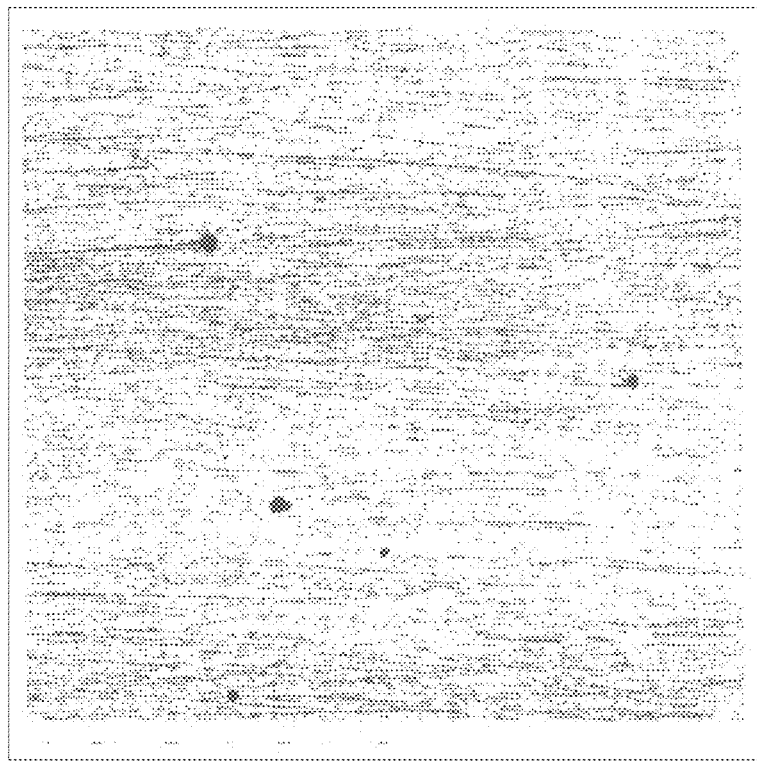
FIG. 3A is a matrix density plot of profilometer data after correction by surface incline, and recording only relative depths deeper than 20 µm.
Figure 3C:
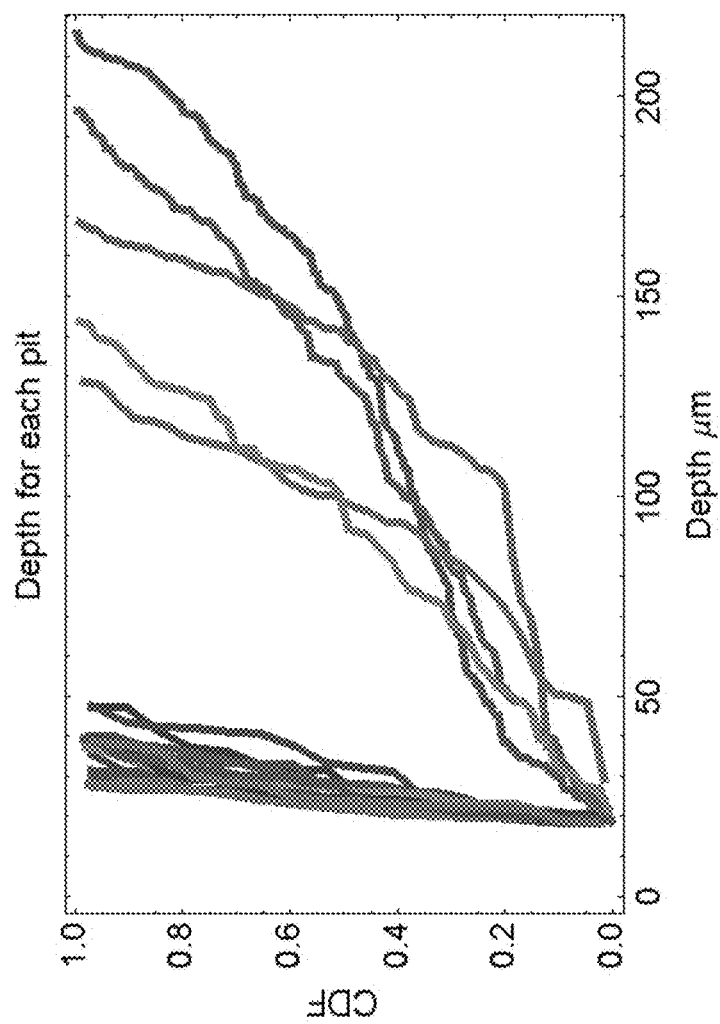
FIG. 3C shows the cumulative distribution function (CDF) of depths for each pit cluster.

FIGS. 3A, 3B, 3C, 3D and 3E illustrate a further example of an approach to filter out pits and features likely associated with surface roughness. FIG. 3A is the matrix density plot of M after correction by surface incline and curvature, and ignoring points satisfying $\Delta z \geq -20$ μm. FIG. 3B is the outcome of the filtration algorithm, $M_3 * M$. FIG. 3C shows the cumulative distribution function (CDF) of depths for each pit cluster (composed of a collection of pixels). A CDF value on the vertical axis is the fraction of the number of pixels with depths less than the depth on the horizontal axis. Each curve in FIG. 3C corresponds to an independent cluster of pixels. Note that a number of CDFs are grouped at values less than 50 μm. These clusters are shallow features, which could be associated with surface features related to roughness or to shallow localized corrosion.

Figure 3D:
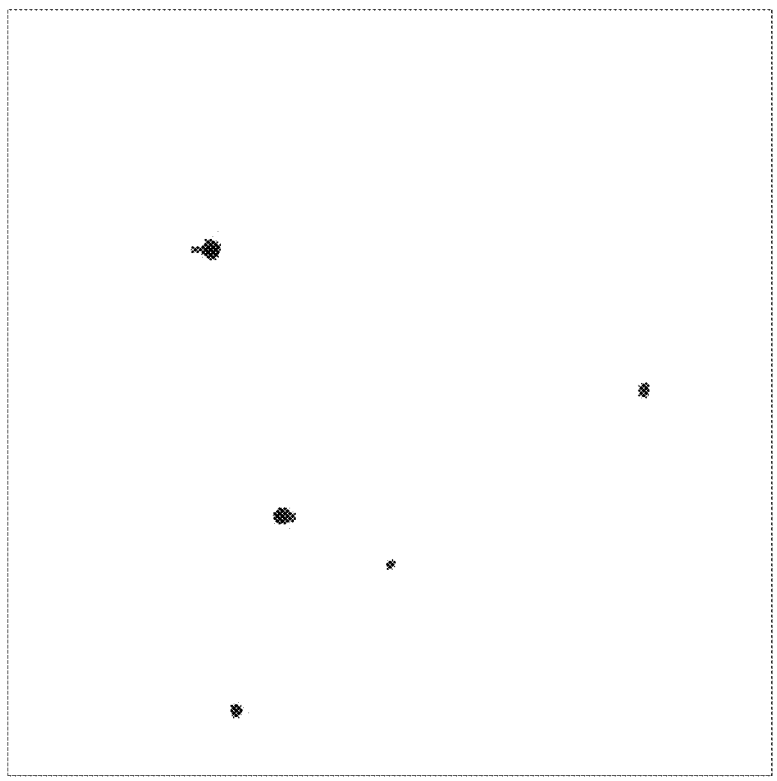
FIG. 3D shows only the pits associated with the 5 CDF curves with the deepest pixels.
Figure 3E:
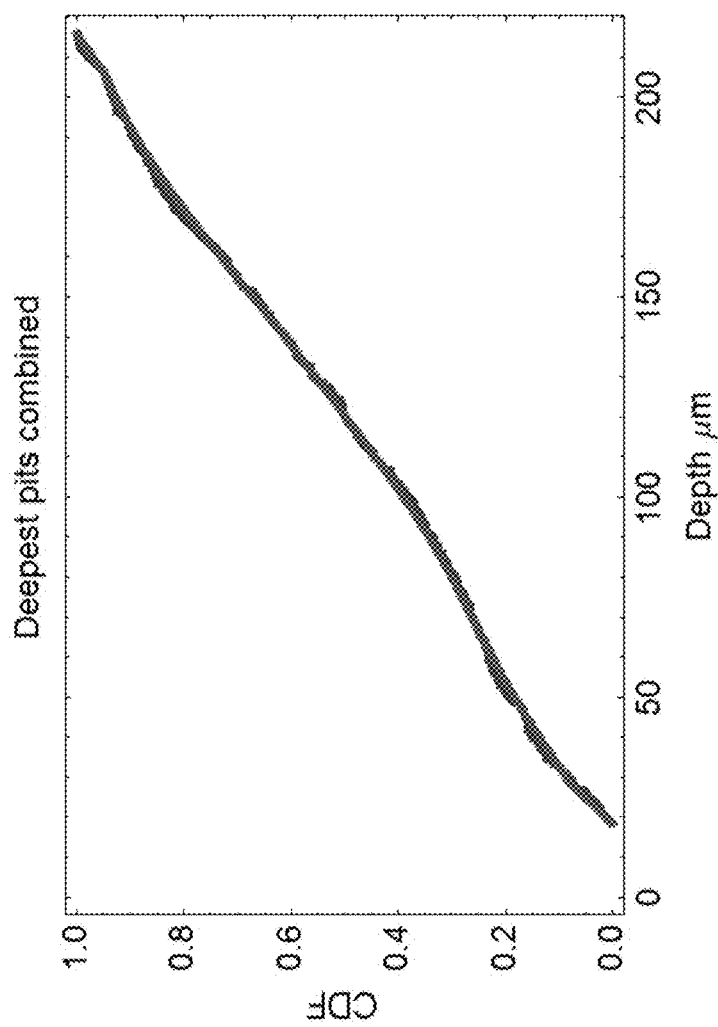
FIG. 3E is the result of combining the 5 deepest clusters of pixels into a single CDF.

FIG. 3D shows only the pits associated with the 5 CDF curves with the deepest pixels [i.e., the 5 CDF curves to the rightmost in the plot in FIG. 3C]. FIG. 3E is the result of combining the 5 deepest clusters of pixels into a single CDF. This combined CDF measures the distribution of pixel depths of the deepest pits. The smooth curve was obtained by the use of a smooth kernel estimator algorithm available in commercial software (Wolfram Mathematica® 8, Wolfram Research, 2011).

Figure 4B:
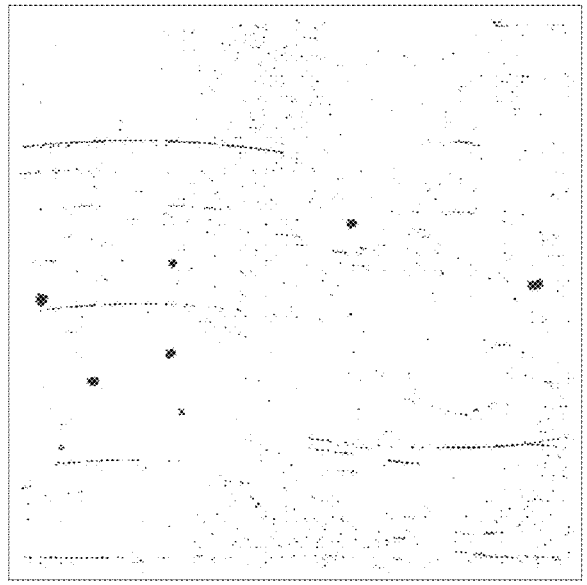
FIGS. 4A, 4B and 4C show an additional example of the 304 SS coupon that was exposed to the indicated environment for 8 days and evaluated according to the method illustrated and described for FIGS. 2A, 2B and 2C.
Figure 4A:
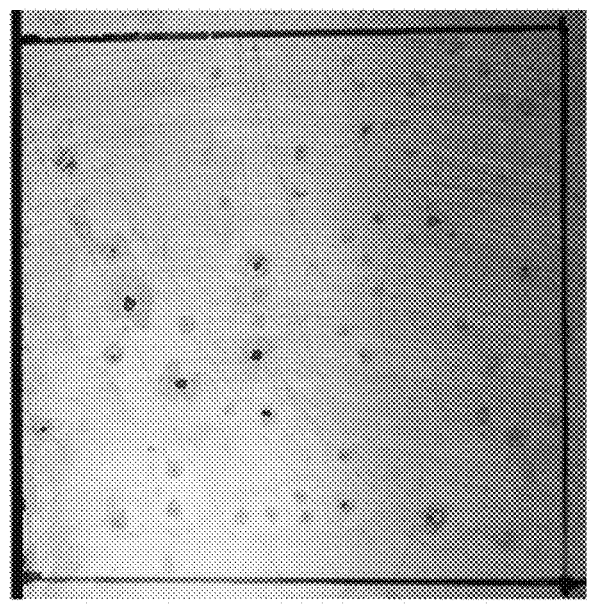
Figure 4C:
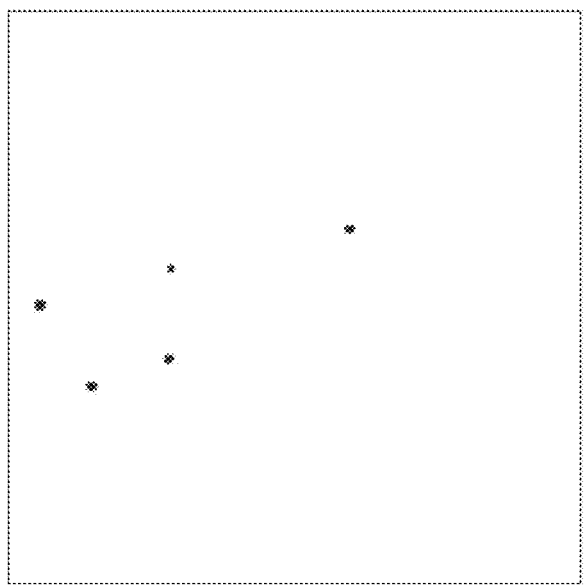
Figure 5B:
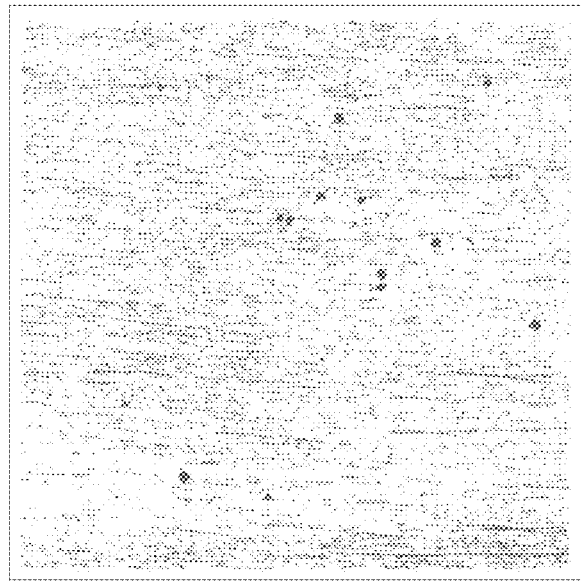
FIGS. 5A, 5B and 5C show an additional example of the 304 SS coupon that was exposed to the indicated environment for 23 days and evaluated according to the method illustrated and described for FIGS. 2A, 2B and 2C.
Figure 5A:
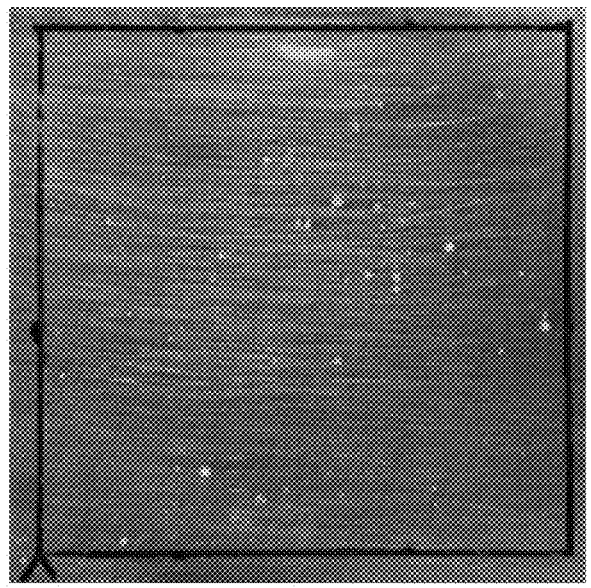
Figure 5C:
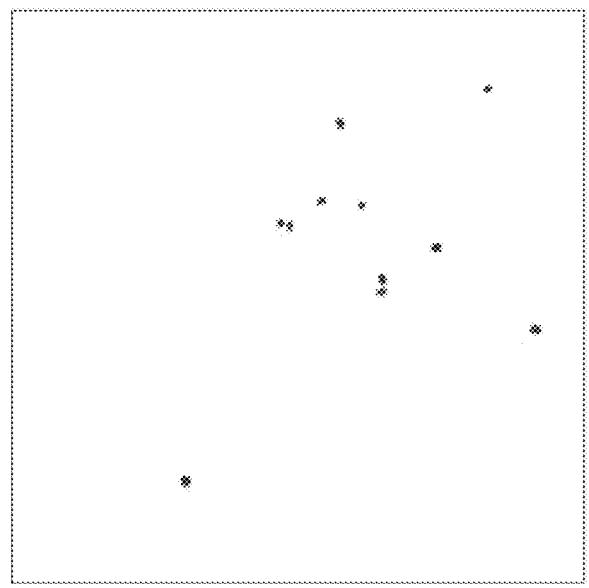
Figure 6B:
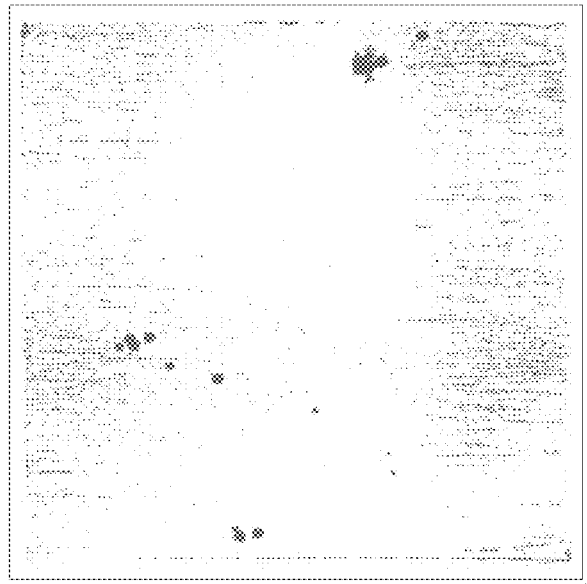
FIGS. 6A, 6B and 6C show an additional example of the 304 SS coupon that was exposed to the indicated environment for 105 days and evaluated according to the method illustrated and described for FIGS. 2A, 2B and 2C.
Figure 6A:
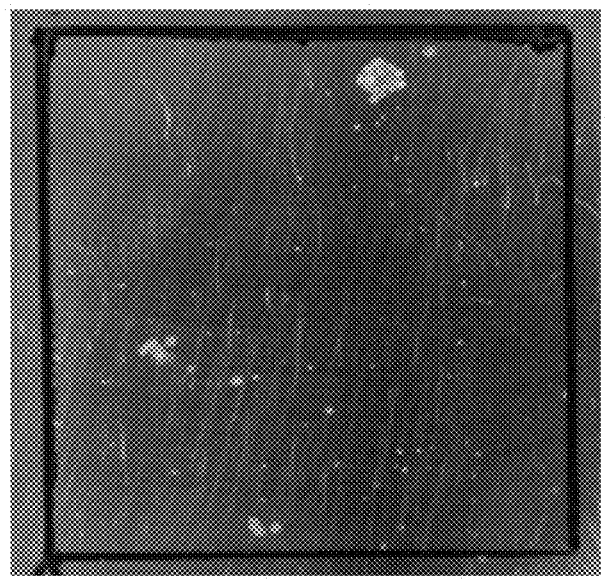
Figure 6C:
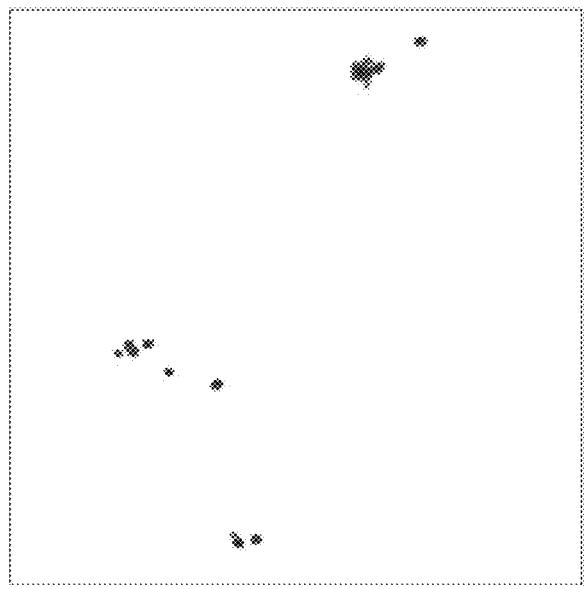
Figure 7B:
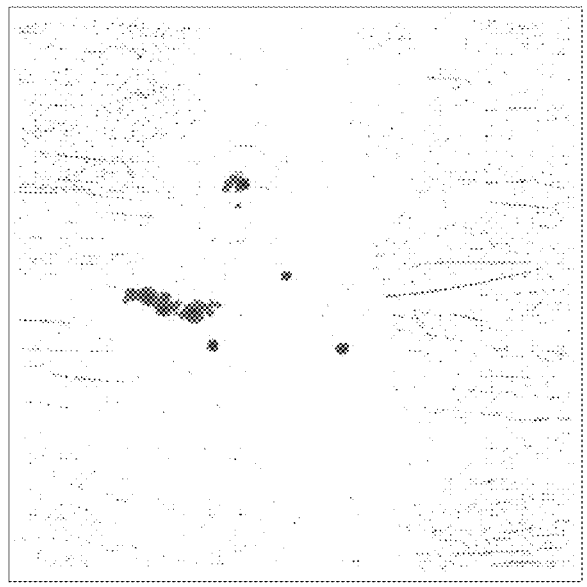
FIGS. 7A, 7B and 7C show an additional example of the 304 SS coupon that was exposed to the indicated environment for 203 days and evaluated according to the method illustrated and described for FIGS. 2A, 2B and 2C.
Figure 7A:
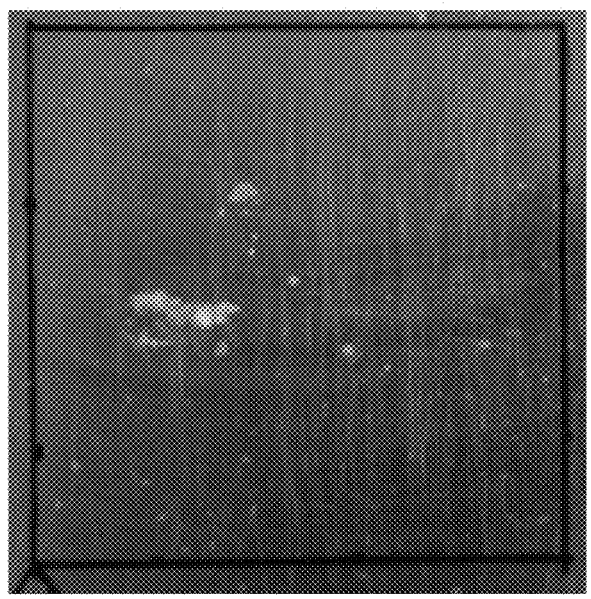
Figure 7C:
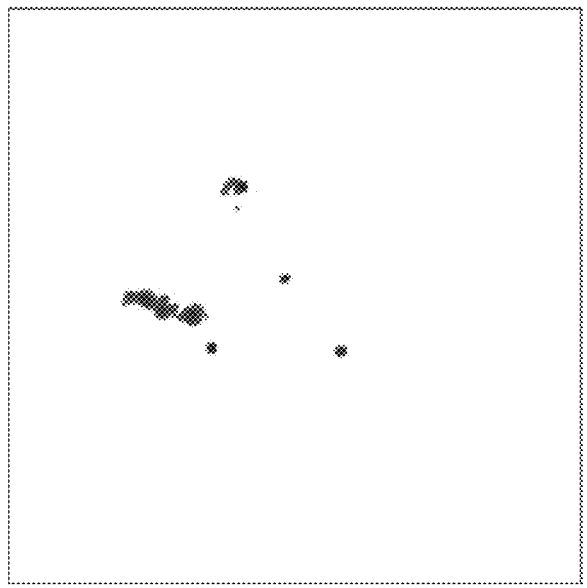

FIGS. 4A, 4B and 4C show an additional example of the 304 SS coupon that was exposed to the above referenced corrosive environment for 8 days. FIGS. 5A, 5B and 5C show an additional example of the 304 SS coupon exposed to the above referenced corrosive environment for 23 days. FIGS. 6A, 6B and 6C show an additional example of the 304 SS coupon exposed to the above referenced corrosive environment for 105 days. FIGS. 7A, 7B and 7C show an additional example of the 304 SS coupon exposed to the above referenced corrosive environment for 203 days.

The method employed in these various figures is the same as the method applied in FIGS. 2A, 2B and 2C noted above. Accordingly, FIGS. 4A, 5A, 6A and 7A are photographs of a 4 cm×4 cm square of the coupon. FIGS. 4B, 5B, 6B and 7B identify the laser profilometer output corrected for surface inclined and ignoring relative depths, $\Delta z$, greater than or equal to −20 μm, presented in the form of density matrix plots. FIGS. 4C, 5C, 6C and 7C identify the filtered image and identification of pits associated only with corrosion after application of equations [8] and [9].

Figure 8B:
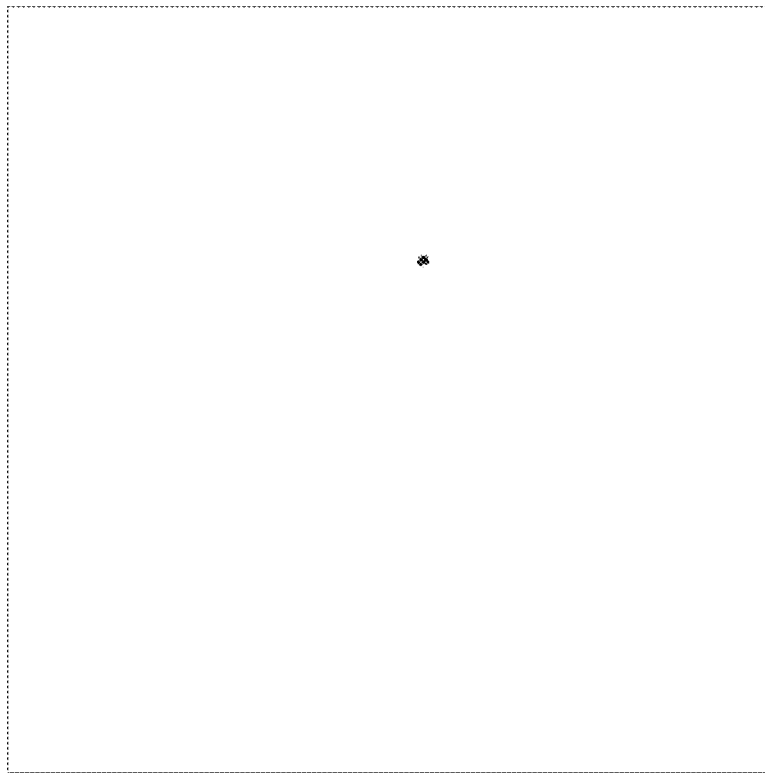
FIG. 8B identifies the deepest pit relative location.
Figure 8A:
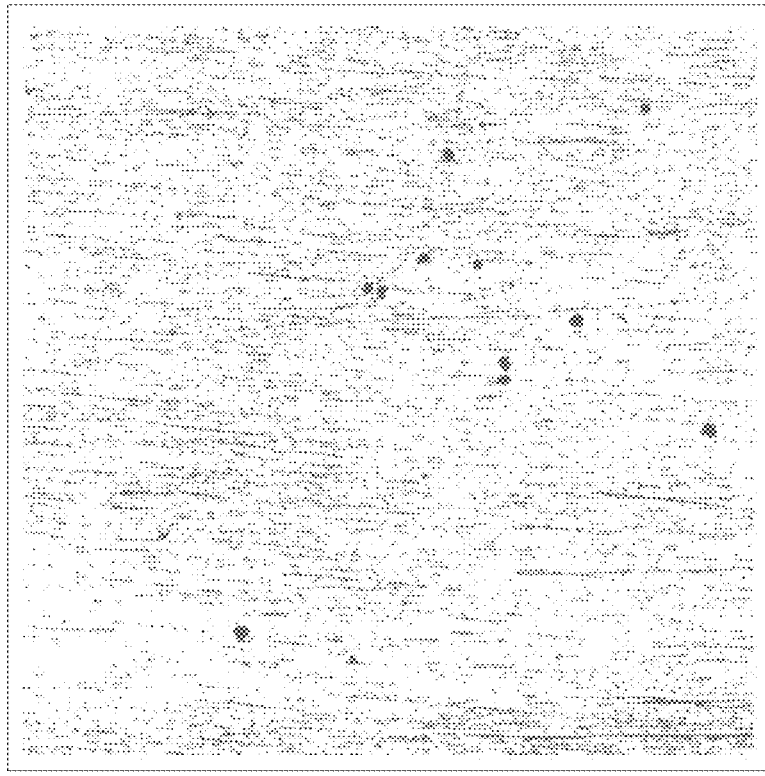
FIG. 8A shows the matrix density plot of the coupon exposed for 23 days.
Figure 8C:
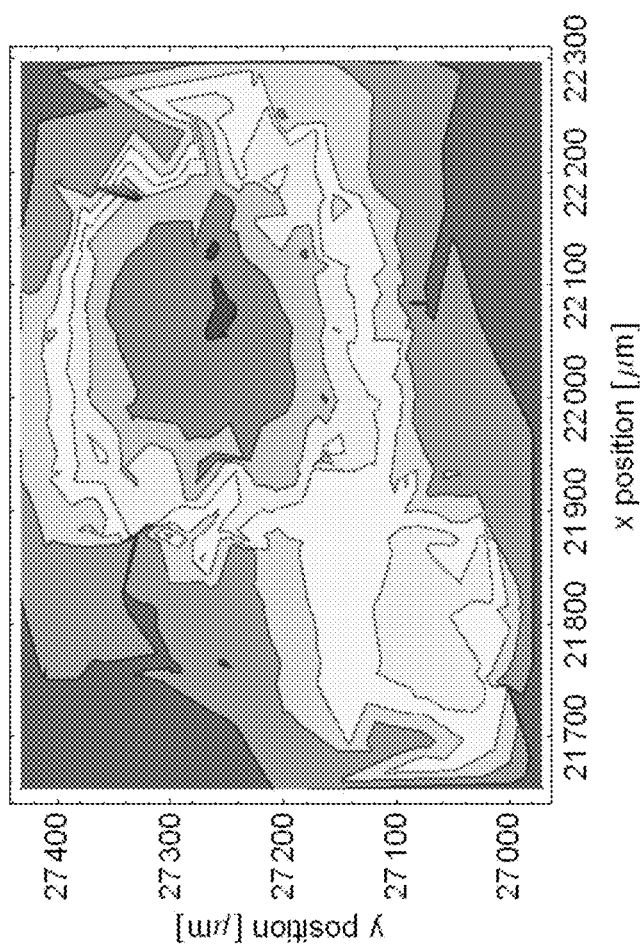
FIG. 8C is a contour plot.
Figure 8D:
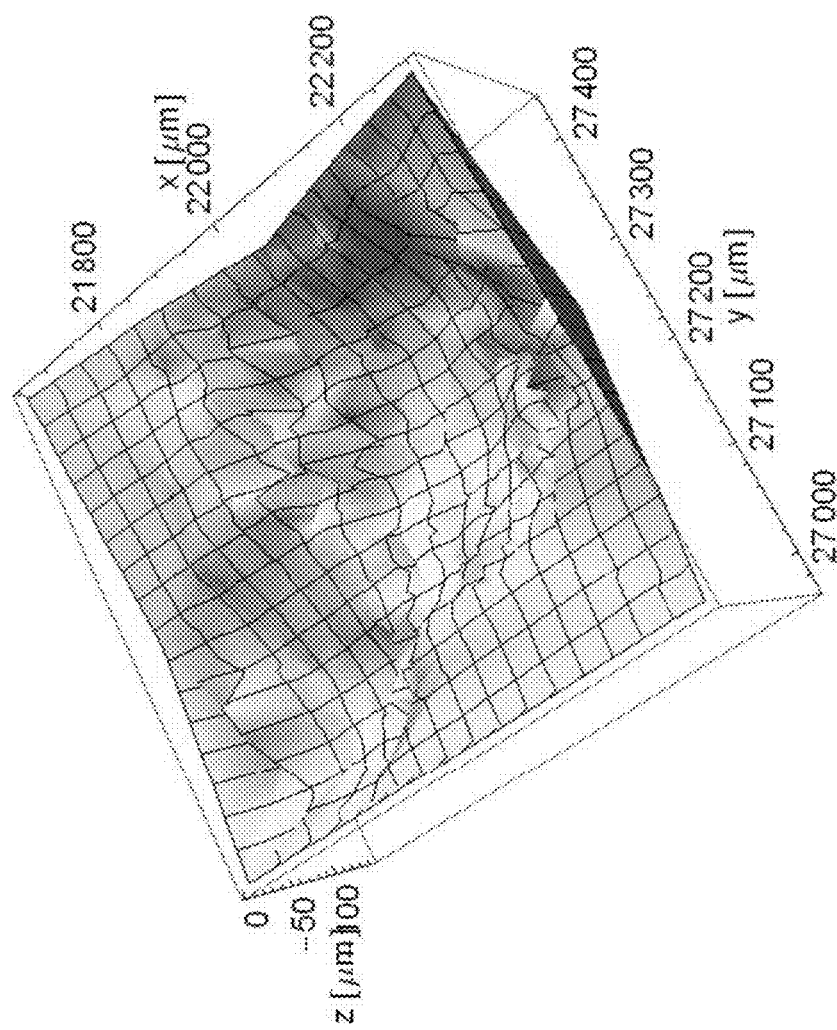
FIG. 8D is 3-dimensional plot of the pit surface
Figure 8E:
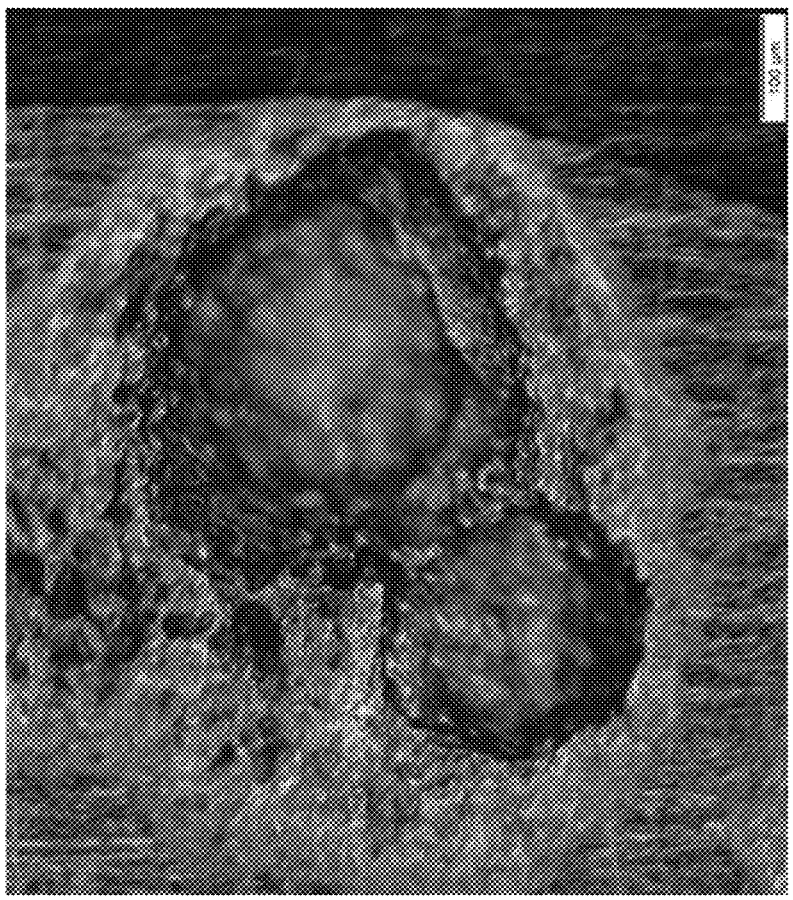
FIG. 8E is a micrograph of the pit.

The filter algorithm herein, summarized in equations [8] and [9] also can be used to "zoom-in" on specific pit clusters, enabling more detailed analysis. An example of the zoom-in approach is presented in FIGS. 8A, 8B, 8C and 8D. Using the CDFs for the cluster depths, as in FIG. 3E the deepest cluster of pixels can be identified. The filter matrix, $M_3$, can be employed to determine the coordinates of the different clusters. For example, FIG. 8A shows the matrix density plot of the coupon exposed for 23 days. FIG. 8B identifies the deepest pit relative location. FIG. 8C is a contour plot and FIG. 8D is a three-dimensional plot of the pit surface from the profilometry readouts. In computing the contour plot and three-dimensional plot, the filter matrix $M_3$ was used to find the precise coordinates of the deepest pit, and extract information from the original profilometry readout file. This technique employing the $M_3$ matrix filter to zoom-in can be used to efficiently analyze each of the pits. FIG. 8E is a micrograph of the pit. The agreement between the profilometry data and the micrograph is reasonable, supporting the conclusion that profilometry data and the pattern recognition algorithm can be used to efficiently characterize corrosion damage by pitting.

Additional information to characterize pitting corrosion is available. For example, the precise number of pixels associated with deep pits is known, and the area of each pixel is known (e.g. 80 μm×80 μm). Therefore, by the product of the number of pixels and the pixel area, the area associated with pitting corrosion can be computed. Since the area and the depths are known, the total metal volume affected by pitting corrosion can be determined.

Embodiments of the methods described herein for evaluating small defects or anomalies on a selected surface may be implemented in a system that includes one or more storage mediums having stored thereon, individually or in combination, instructions that when executed by one or more processors perform the identified methods. Here, the processor may include, for example, a system CPU (e.g., core processor) and/or programmable circuitry. Thus, it is intended that operations according to the methods described herein may be distributed across a plurality of physical devices, such as, for example, processing structures at several different physical locations. Also, it is intended that the method operations may be performed individually or in a subcombination, as would be understood by one skilled in the art. Thus, not all of the operations of each step of the above methodology need to be performed, and the present disclosure expressly intends that all subcombinations of such methods are enabled as would be understood by one of ordinary skill in the art.

The storage medium may include any type of tangible medium, for example, any type of disk including floppy disks, optical disks, compact disk read-only memories (CD-ROMs), compact disk rewritables (CD-RWs), digital versatile disks (DVDs) and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions.

While the present invention has been described and illustrated above with references to exemplary embodiments, it should be understood that various modifications could be made without departing from the scope of the invention. Therefore, the invention is not to be limited to the exemplary embodiments described and illustrated above.

The invention claimed is:

1. A computer-implemented method for identifying corrosion surface pits on a metal surface comprising:
receiving, by a processor, measurements corresponding to a plurality of pits on the metal surface from a profilometer, said measurements including a value of x, y, and z for each pit of said plurality of pits, where x and y are positions on the metal surface and z is the depth, wherein said metal surface has a surface incline and curvature;
correcting, by the processor, for the presence of surface incline and curvature by initially fitting the values of x, y, and z into the following relationship:

$$z_{plane}(x,y) = a + bx + cx^2 + dy + ey^2 + fxy \qquad (1)$$

wherein the coefficients a, b, c, d, e and f are all real numbers and vary according to the incline and curvature of the metal surface;
identifying, by the processor, a collection of differences, $\Delta z = z_{meas} - z_{plane}$, that satisfy the expression below $$|\Delta z| = |z_{meas} - z_{plane}| \leq z_o$$

where $z_{meas}$ is the measured value of the z coordinate at a given x, y location on the metallic surface and $z_{plane}$ is the value of z at that location according to equation (1), and $z_o$ is assigned a depth value ($=-d_{pit}$) that is selected to compensate for the precision of the profilometer and the surface roughness present and not due to corrosion;
mapping of pit depths, by the processor, that are less than $d_{pit}$ into a two-dimensional matrix of pixels (M), wherein a value of $\Delta z$ of greater than $d_{pit}$ is ignored and an associated pixel is assigned a value of zero, and a value of $\Delta z$ of less than $d_{pit}$ is entered and mapped into said two-dimensional matrix of pixels (M);
identifying, by the processor, pit depths in said two-dimensional matrix of pixels (M) associated with corrosion by mapping a group of spikes within proximity of each other based on corresponding pixel values;
identifying, by the processor, pit depths in said two-dimensional matrix of pixels (M) associated with surface roughness based on isolated spikes represented within corresponding pixel values; and
producing a view of the metal surface that visually identifies a relative position of the identified pit depths associated with corrosion.

2. The method of claim 1 wherein mapping of pit depths further comprises mapping said two-dimensional matrix of pixels (M) into a second matrix ($M_2$) according to the following:

$$M_2 = |Sign(M)|$$

where said Sign function is applied to said entries in said matrix M to generate matrix $M_2$ wherein matrix $M_2$ entries are either zero (0) which correspond to zero entries in $M_1$ and $M_2$ entries of one (1) correspond to non-zero entries in $M_1$; and
applying a moving average to the one (1) entries in $M_2$ to identify clusters of one (1) entries in M associated with pits due to corrosion.

3. The method of claim 1 wherein said profilometer is a laser profilometer.

4. The method of claim 1 wherein: $-20 \, \mu m \leq \Delta z \leq 20 \, \mu m$.

5. The method of claim 1 wherein said metal surface comprises a metal coupon exposed to a corrosion environment.

6. A system for identifying corrosion surface pits on a metal surface comprising:
a profilometer that provides output information identifying a plurality of pits on said metal surface and assigns said plurality of pits a value of x, y, and z where x and y are positions on the metal surface and z is the depth, wherein said metal surface has a surface incline and curvature;
a processor connected to receive said output from said profilometer to:
correct for the presence of surface incline and curvature by initially fitting the values of x, y, and z into the following relationship:

$$z_{plane}(x,y) = a + bx + cx^2 + dy + ey^2 + fxy \qquad (1)$$

wherein the coefficients a, b, c, d, e and f are all real numbers and vary according to the incline and curvature of the metal surface;
identify a collection of differences, $\Delta z = z_{meas} - z_{plane}$, that satisfy the expression below $$|\Delta z| = |z_{meas} - z_{plane}| \leq z_o$$

where $z_{meas}$ is the measured value of the z coordinate at a given x, y location on the metallic surface and $z_{plane}$ is the value of z at that location according to equation (1), and $z_o$ is assigned a depth value ($=-d_{pit}$) that is selected to compensate for the precision of the profilometer and the surface roughness present and not due to corrosion;
map pit depths that are less than $d_{pit}$ into a two-dimensional matrix of pixels (M) wherein a value of $\Delta z$ of greater than $d_{pit}$ is ignored and an associated pixel is assigned a value of zero and a value of $\Delta z$ of less than $d_{pit}$ it is entered and mapped into said two-dimensional matrix of pixels (M); and
identify pit depths in said two-dimensional matrix of pixels (M) associated with corrosion by mapping a group of spikes within proximity of each other based on corresponding pixel values;
identify pit depths in said two-dimensional matrix of pixels (M) associated with surface roughness based on isolated spikes represented within corresponding pixel values; and
produce a view of the metal surface that visually identifies a relative position of the identified pit depths associated with corrosion.

7. The system of claim 1 wherein mapping pit depths that are less than $d_{pit}$ into a two-dimensional matrix of pixels (M) pit depths further comprises mapping said two-dimensional matrix into a second matrix ($M_2$) according to the following:

$$M_2 = |\text{Sign}(M)|$$

where said Sign function is applied to said entries in said matrix M to generate matrix $M_2$ wherein matrix $M_2$ entries are either zero (0) which correspond to zero entries in $M_1$ and $M_2$ entries of one (1) correspond to non-zero entries in $M_1$; and applying a moving average to the one (1) entries in $M_2$ to identify clusters of one (1) entries in M associated with pits due to corrosion.

8. The system of claim 1 wherein said profilometer is a laser profilometer.

9. The system of claim 1 wherein: $-20 \ \mu m \leq \Delta z \leq 20 \ \mu m$.

10. The system of claim 1 wherein said metal surface comprises a metal coupon exposed to a corrosion environment.

* * * * *